United States Patent
Marten et al.

(10) Patent No.: US 6,328,754 B1
(45) Date of Patent: Dec. 11, 2001

(54) NASAL DILATOR

(75) Inventors: Lewis H Marten, Westwood; Anthony M Sacchetti, Quincy, both of MA (US)

(73) Assignee: E. Benson Hood Laboratories, Pembroke, MA (US)

( * ) Notice: Subject to any disclaimer, the term of this patent is extended or adjusted under 35 U.S.C. 154(b) by 0 days.

(21) Appl. No.: 09/566,032

(22) Filed: May 8, 2000

(51) Int. Cl.⁷ .................................................... A61M 29/00
(52) U.S. Cl. ............................................................ 606/199
(58) Field of Search ..................................... 606/196, 199, 606/198–204.45; 128/200.24, 200.25, 207.18, 858, 200.26

(56) References Cited

U.S. PATENT DOCUMENTS

| D. 310,565 | 9/1990 | Petruson . |
| 1,709,740 | 4/1929 | Rogers . |
| 1,950,839 | 3/1934 | Chirila . |
| 3,710,799 | 1/1973 | Caballero . |
| 4,201,217 | 5/1980 | Slater . |
| 4,414,977 | 11/1983 | Rezakhany . |
| 5,479,944 | * 1/1996 | Petruson .............................. 606/196 |
| 5,922,006 | * 7/1999 | Sugerman ...................... 606/204.45 |

* cited by examiner

Primary Examiner—Henry J. Recla
Assistant Examiner—Kevin Truong
(74) Attorney, Agent, or Firm—Pitney, Hardin, Kipp & Szuch, LLP

(57) ABSTRACT

A device for dilating nasal passageway which includes a resilient bar having pads on opposite ends for insertion into respective nasal passageways and the bar when bent causes a biasing outward force on the pads to dilate the anterior section of the nasal cavity with said bar having notches thereon which can be selectively cut to reduce the bearing force on the pads.

12 Claims, 2 Drawing Sheets

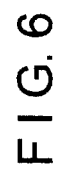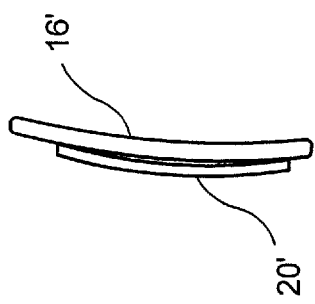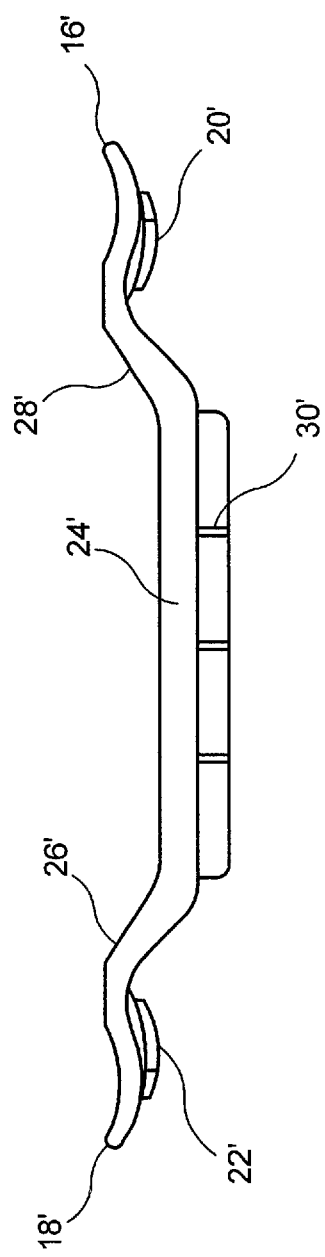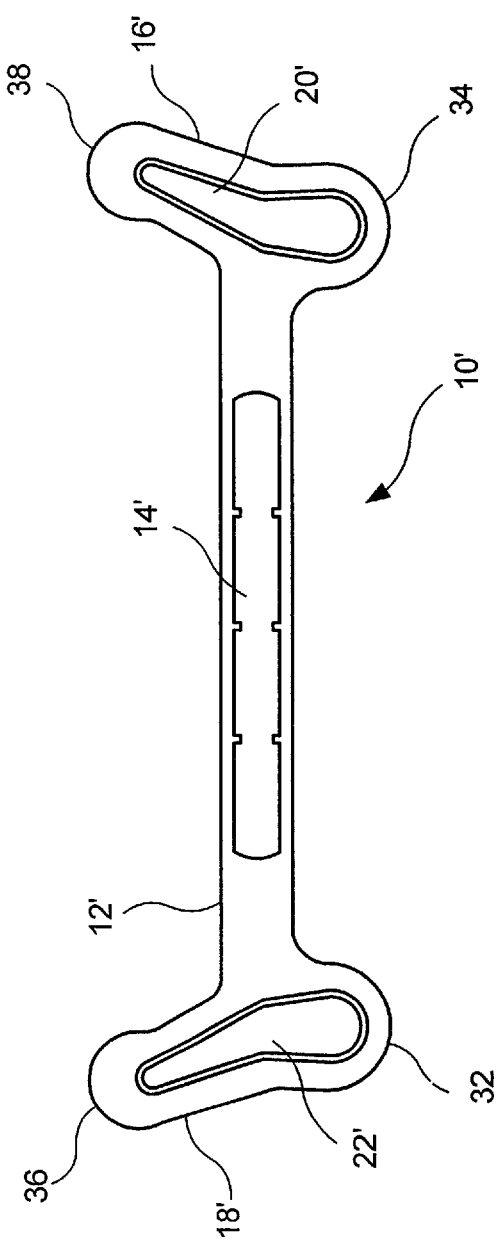

NASAL DILATOR

FIELD OF THE INVENTION

The invention is directed towards a device for facilitating respiration or breathing.

BACKGROUND OF THE INVENTION

The present device is of the type used to expand the air passages in nostrils. Such devices have been used in the past to improve breathing, eliminate or reduce snoring or as surgical aid among other things.

Devices which have been used in this regard include U.S. Pat. No. 1,709,740 issued Apr. 16, 1929 to Rogers. This reference shows the use of a nasal distender using a wire bridge between two u-shaped members which contact the inner walls of the nose.

In U.S. Pat. No. 1,950,839 issued Mar. 13, 1934 to Cherila discloses a dilator using a metal bridge between two suction members attached to the outside of the nostrils to pull them outward keeping the nostrils open.

With regard to U.S. Pat. No 3,710,799 issued Jan. 16, 1973 to Caballero, it discloses a pair of spherical cages for insertion into the nostrils which are joined by a chain. In U.S. Pat. No. 4,201,217 issued May 6, 1980 to Slater, there is disclosed a nostril enlarger having a u-shaped member having opposite posterior protuberances biased outwardly for positioning in the nostril cavity. A bridge therebetween is the opposite protuberances apart the proper distance.

U.S. Pat. No. 4,414,977 issued Nov. 15, 1983 to Rezakhany shows another variation of a nasal dilator. Lastly, U.S. Design Pat. No. 310,565 issued Sep. 11, 1990 to Petruson shows a device for insertion into the nose having two end portions having raised protuberances interconnected by a bridge.

While all of the foregoing devices have attendant advantages and disadvantages, there exist a need to provide for a nasal dilator which is relatively simple yet effective whilst allowing for the device to be tailored for the particular individual using it.

SUMMARY OF THE INVENTION

It is a principal object of the invention to provide for a nasal dilator which is relatively simple yet effective.

It is a further object of the invention to provide for a nasal dilator that can be readily adjusted so as to allow it to be tailored to a particular individual.

The present invention provides for a nasal dilator which is made of plastic or silicone and comprises opposite curved pads located at the ends of a resilient bar having a center member thereon. The dilator is flexible with the pads squeezed together for insertion into respective nostrils. The resilient bar and centering member then biases the pad outward so as to dilate the anterior section of the nasal cavity. Included on the centering member are a series of notches one or more of which can be cut so as to reduce the biasing nature of the centering member thereby allowing the force of the device to be adjusted for varying needs of the individual.

BRIEF DESCRIPTION OF THE DRAWINGS

Thus by the present invention its objects and advantages will be realized, the description of which should be taken in conjunction with the drawings wherein:

FIG. 4 is a top plan view of another embodiment of the nasal dilator incorporating the teachings of the present invention;

FIG. 5 is a top side view of the nasal dilator shown in FIG. 4; and

FIG. 6 is a side view of the pad portion of the nasal dilator shown in FIGS. 4 and 5.

DETAILED DESCRIPTION OF THE PREFERRED EMBODIMENT

Figure 3:
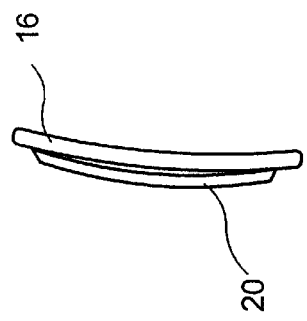
FIG. 3 is a side view of the pad portion of the nasal dilator shown in FIGS. 1 and 2.
Figure 1:
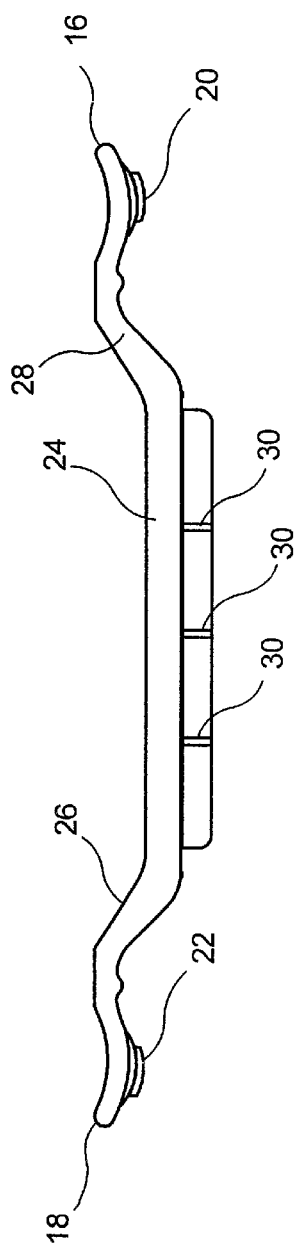
FIG. 1 is a top plan view of the nasal dilator incorporating the teachings of the present invention.
Figure 2:
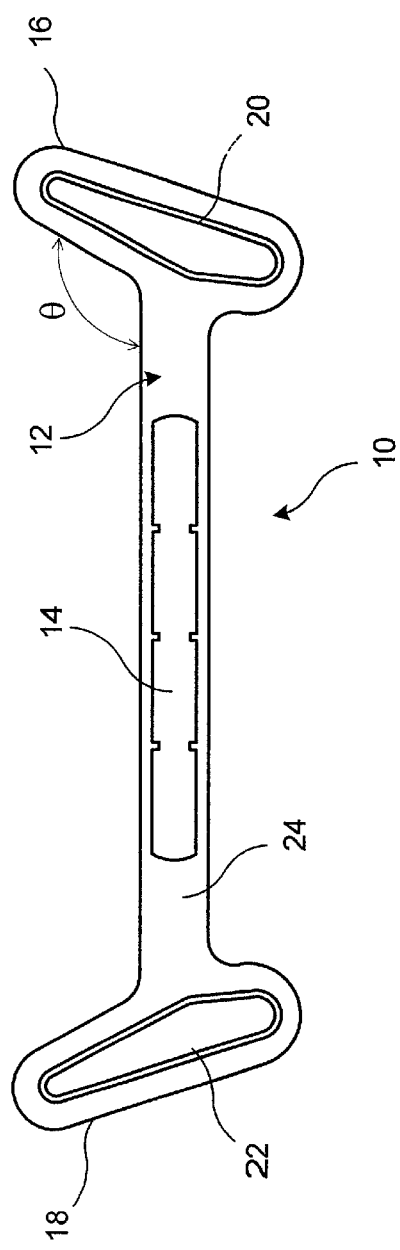
FIG. 2 is a top side view of the nasal dilator shown in FIG. 1.

Turning now more particularly to the drawings, there is shown in the FIGS. 1–3 a nasal dilator which may be integrally constructed out of a suitable plastic material (eg. soft, clear and resilient), silicone of approximately 50–70 durometer or other material suitable for purpose. The characteristics of the material used should allow the device to be flexible and resilient as will more fully become apparent. The dilator 10 included an elongated resilient bar having a center member 14 thereon. The bar 12 has positioned on its opposite ends slightly curved pads 16 and 18. The pads 16 and 18 have a radius on the x-axis and y-axis and are of a somewhat triangular shape which match the appropriate anatomy of the anterior section of the nasal cavity. This provides a comfortable fit and ease in conforming to the interior shape of the nostrils. The shape of the pads 16 and 18 force a user to insert the upper ends of the pad first, then lock them into place by inserting the lower end of the pad. Included on the pads 16 and 18 are respective raised ridge portions 20 and 22.

The resilient bar 12 includes a somewhat straight portion 24 and respective angled portions 26 and 28 which are seen most clearly in FIG. 2 terminate in the pad 16 and 18.

The center member 14 traverses the resilient bar 12, is centrally located thereon, and may be made of the same material as bar 12. Included on member 14 are a plurality of notches 30.

In use, the dilator 10 is resiliently bent into a u-shape and the pad members 16 and 18 inserted into respective nasal cavities. Bar 12 causes an outwardly bearing force on pads 16 and 18 so as to dilate the anterior section of the nasal cavity. Pads 16 and 18 are held rigid by the ridges 20 and 22 bordering the pads. The ridges 20 and 22 also prevent the device from slipping. The angle of the pads 16 and 18, (which is approximately 115° from the longitudinal axis of the bar 12) also position the resilient bar 12 against the skin above the upper lip. The pads will remain stable in the anterior section of the nasal cavity once positioned, as a result of the angle (i.e. approximately 115°), the triangular shape, the curvature, and the circumferential ridges 20 and 22.

In that the resiliency of bar 12 causes the bearing force on the pads 16 and 18 and the center member 14 is a part thereof, a cutting or fracturing of one or more of the notches 30 will reduce the bearing force on the pads 16 and 18. Thus depending upon the number of notches 30 cut, the desired bearing force can be adjusted so as to accomodate the needs or comfort of the particular individual using it.

As to the overall dimensions of the dilator 10, its length is approximately 3", width 0.20" with the center bar being approximately 1.34", and a width of 0.13" and the notches have a dimension of 0.5 mm×0.5 mm. These dimensions are by no means exclusive but rather illustrate as an example the dimensions the dilator 10 may have.

Turning now to FIGS. 4–6, like parts are similarly numbered with, however, a prime. The nasal dilator 10' is the same as that shown in FIGS. 1–3 except that wings or increased portions 32, 34, 36 and 38 have been added to pads 16' and 18'. These tend to increase the stability of the dilator 10' in larger nostrils and reduce the possibility of slipping out of position. The pads 16' and 18' are approximately 20% larger than pads 16 and 18. In all other respects (except for a slight configuration of ridge portions 20' and 22'), the dilators 10 and 10' are the same.

Thus by the present invention its objects and advantages are realized and, although a preferred embodiment has been disclosed and described in detail herein, its scope should not be limited thereby rather its scope should be determined by that of the appended claims wherein:

What is claimed is:

1. A device for dilating nasal passageways comprising:
   an elongated bar portion made of a resilient material, having opposite ends;
   respective pads positioned on said opposite ends for positioning in respective nasal passageways;
   said bar portion when in a bent position providing an outwardly bearing force on said pads which causes said pads to engage and dilate the nasal passageways when disposed therein; and
   said bar portion further comprising at least one indicating means thereon which when cut or fractured reduces the bearing force provided by the bar on the pads so as to allow for an adjustment thereof.

2. The device in accordance with claim 1 wherein said pads are curved and somewhat triangular in shape.

3. The device in accordance with claim 2 wherein said pads are disposed at an angle of approximately 115° to a longitudinal axis of the bar.

4. The device in accordance with claim 3 which further includes respective ridge members on said pads.

5. The device in accordance with claim 2 wherein said pads include enlarged portions for increased stability when placed in nasal passageways.

6. The device in accordance with claim 1 which includes a center member traversing the bar on which said indicating means is located.

7. The device in accordance with claim 6 wherein said indicating means comprises a plurality of notches.

8. The device in accordance with claim 7 wherein said device is integrally constructed from a resilient plastic or silicone material.

9. The device in accordance with claim 8 wherein the resilient plastic or silicone material is approximately 50–70 durometers.

10. The device in accordance with claim 1 wherein said indicating means comprises a plurality of notches.

11. The device in accordance with claim 1 wherein said device is integrally constructed from a resilient plastic or silicone material.

12. The device in accordance with claim 11 wherein the resilient plastic or silicone material is approximately 50–70 durometers.

* * * * *